United States Patent
Laser et al.

(10) Patent No.: US 12,076,254 B2
(45) Date of Patent: Sep. 3, 2024

(54) EXPANDING DEVICES FOR ENDOLUMINAL INTERVENTIONS

(71) Applicant: Myka Labs, Inc., San Francisco, CA (US)

(72) Inventors: Daniel J. Laser, San Francisco, CA (US); Robert H. Grubbs, South Pasadena, CA (US)

(73) Assignee: Myka Labs, Inc., San Francisco, CA (US)

( * ) Notice: Subject to any disclaimer, the term of this patent is extended or adjusted under 35 U.S.C. 154(b) by 0 days.

(21) Appl. No.: 17/985,847

(22) Filed: Nov. 12, 2022

(65) Prior Publication Data
US 2023/0149188 A1    May 18, 2023

Related U.S. Application Data

(60) Provisional application No. 63/279,030, filed on Nov. 12, 2021.

(51) Int. Cl.
| | |
|---|---|
| *A61F 2/82* | (2013.01) |
| *A61B 17/11* | (2006.01) |
| *A61F 2/958* | (2013.01) |
| *A61B 17/00* | (2006.01) |

(52) U.S. Cl.
CPC .............. *A61F 2/82* (2013.01); *A61B 17/1114* (2013.01); *A61F 2/958* (2013.01); *A61B 2017/00876* (2013.01); *A61F 2210/009* (2013.01)

(58) Field of Classification Search
CPC .............. A61F 2/82; A61F 2/958; A61F 17/11
See application file for complete search history.

(56) References Cited

U.S. PATENT DOCUMENTS

| | | |
|---|---|---|
| 8,142,454 B2 | 3/2012 | Harrison et al. |
| 2015/0351730 A1 | 12/2015 | Stokes et al. |
| 2016/0213461 A1 | 7/2016 | Demehri et al. |
| 2020/0297979 A1 | 9/2020 | Heister |
| 2021/0177355 A1 | 6/2021 | Govari |

FOREIGN PATENT DOCUMENTS

| | | |
|---|---|---|
| WO | WO 2007/101526 A1 | 9/2007 |
| WO | WO 2012/007044 A1 | 1/2012 |
| WO | WO 2021/101622 A1 | 5/2021 |

OTHER PUBLICATIONS

PCT International Search Report and Written Opinion, PCT Application No. PCT/US22/79815, dated Apr. 24, 2023, 18 pages.
PCT Invitation to Pay Additional Fees, PCT Application No. PCT/US22/79815, dated Feb. 3, 2023, two pages.

*Primary Examiner* — Matthew W Schall
(74) *Attorney, Agent, or Firm* — Fenwick & West LLP

(57) ABSTRACT

A dual-flange stent can have a therapeutic effect that can bring about a marked increase in patency. The dual flanges of the stent can comprise a first discrete flange component and a second discrete flange component. One or both flange components can include a magnetic element. The stent can further comprise a shaft connecting the flange components. At least one of the flanges can transition between a first configuration and a second configuration, where the first configuration is compact and the second configuration provides a large tissue-compressing surface. In one instance, the transition to the configuration with a large tissue-compressing surface can include filling a balloon with saline or another fluid. The first flange and the second flange may be drawn together to compress interposed tissue of the stricture.

10 Claims, 18 Drawing Sheets

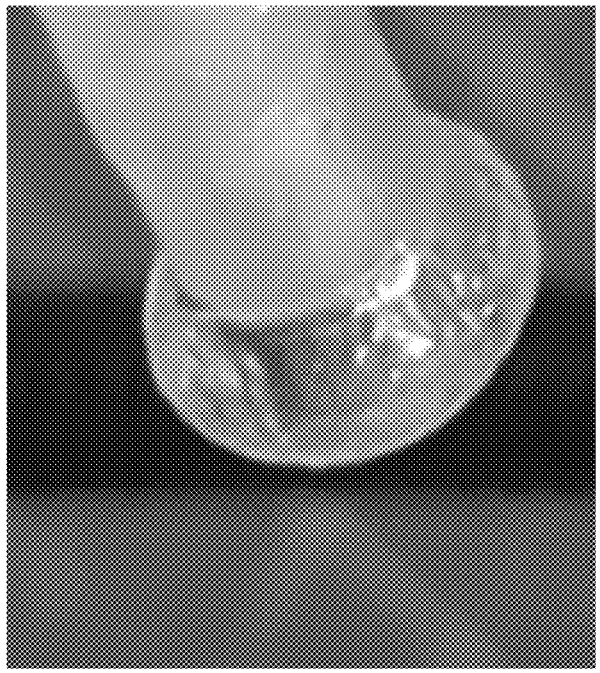
FIG. 12

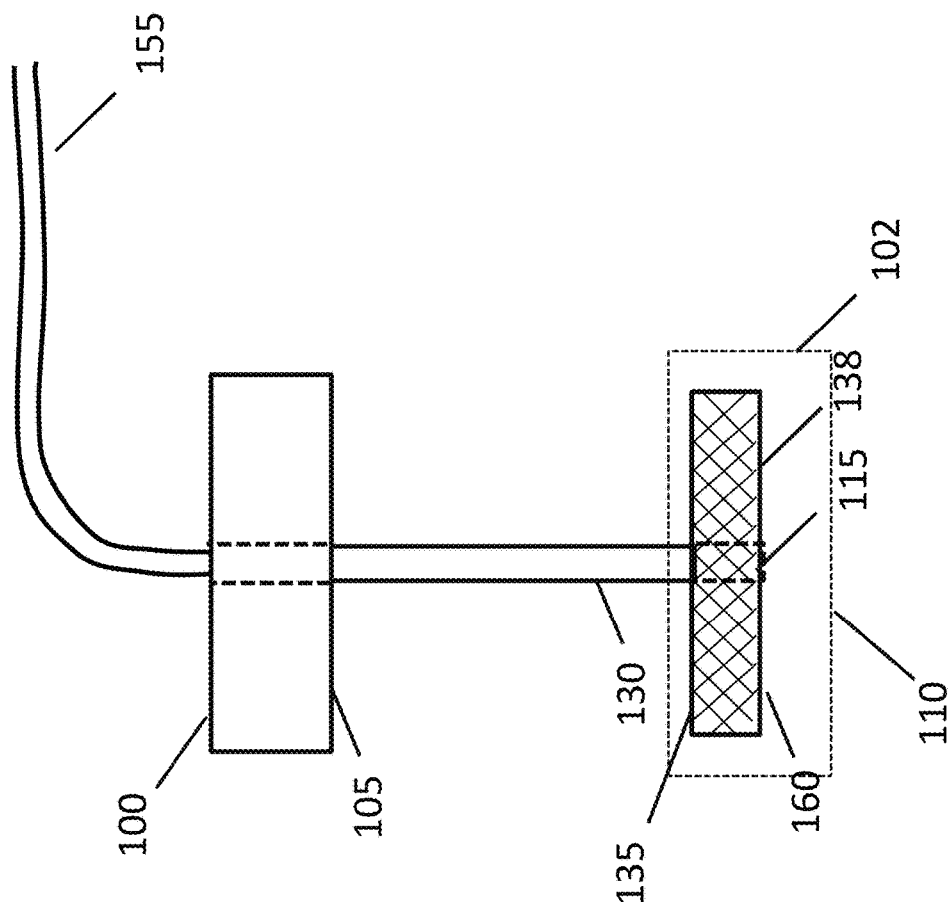

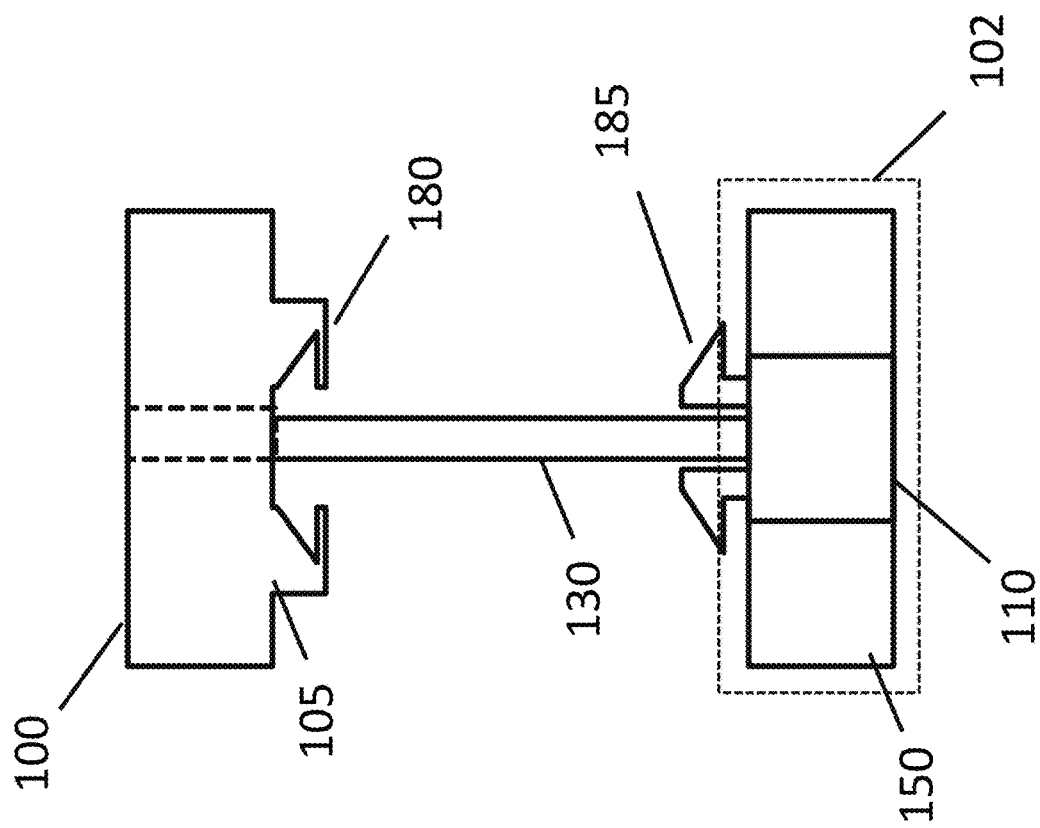

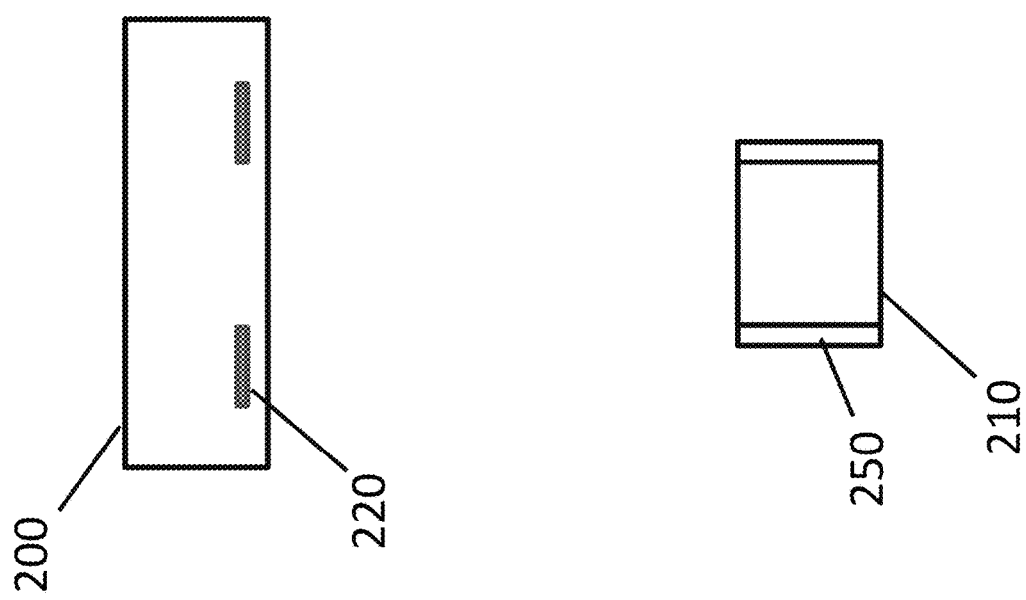

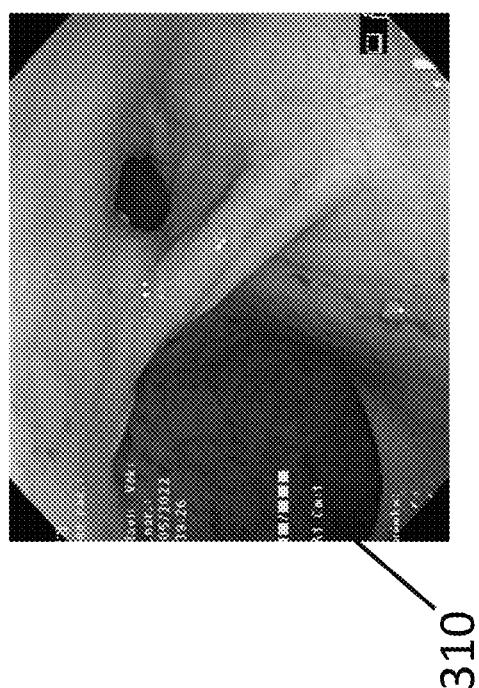
FIG. 18

EXPANDING DEVICES FOR ENDOLUMINAL INTERVENTIONS

CROSS REFERENCE TO RELATED APPLICATIONS

This application claims the benefit of U.S. Provisional Application No. 63/279,030, filed on Nov. 12, 2021, which is incorporated by reference herein in its entirety.

BACKGROUND

Esophageal stricture (ES) is a luminal narrowing from scar tissue, causing dysplasia. Strictures can also occur elsewhere in the gastrointestinal tract and in other organ systems, such as the urinary tract. For example, in patients with Crohn's disease, strictures are common and they may include both de novo strictures as well as strictures arising subsequent to an earlier resection. In Crohn's disease, a resection is often performed around the ileocecal valve, and a stricture can arise at the site of an anastomosis performed to rejoin the two sections of the bowel after the resection. Atresia can occur in the gastrointestinal tract. Current limitations in methods of treating atresias and strictures can negatively affect a patient health for reasons including frequent and persistent recurrence of stricture.

BRIEF DESCRIPTION OF THE DRAWINGS

The teachings of the embodiments can be readily understood by considering the following detailed description in conjunction with the accompanying drawings.

FIG. 12 illustrates a photograph of a device with a balloon, according to one or more embodiments.

FIG. 14 illustrates a dual flange device comprising a wire mesh with an expanded configuration, according to one or more embodiments.

FIG. 15 illustrates a dual flange device comprising a latching mechanism, according to one or more embodiments.

FIG. 16 illustrates a stricture treatment device with integrated force sensors, according to an embodiment, according to one or more embodiments.

FIG. 18 illustrates the results of treating a stricture in a porcine model using longitudinal compression.

DETAILED DESCRIPTION OF EMBODIMENTS

Figure 1B:
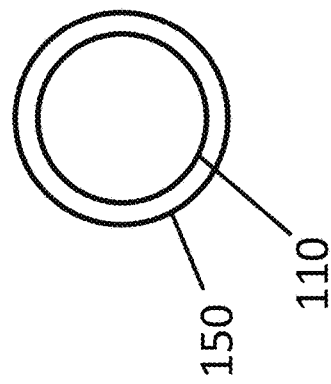
FIGS. 1A AND 1B illustrate a dual-flange stent with a first flange comprising a magnetic element and a second flange comprising a magnetic element and a balloon, where a balloon is positioned circumferentially on a magnetic element and where deflating a balloon can facilitate passing the second flange through a stricture, according to one or more embodiments.

The Figures (FIG.) and the following description relate to preferred embodiments by way of illustration only. It should be noted that from the following discussion, alternative embodiments of the structures and methods disclosed herein will be readily recognized as viable alternatives that may be employed without departing from the principles of the embodiments.

Reference will now be made in detail to several embodiments, examples of which are illustrated in the accompanying figures. It is noted that wherever practicable, similar or like reference numbers may be used in the figures and may indicate similar or like functionality. The figures depict embodiments for purposes of illustration only.

Stricture is a luminal narrowing, often associated with scar tissue. Esophageal stricture (ES) is a stricture in the esophagus. When ES persists or recurs despite multiple (>5) endoscopic balloon dilations—the cornerstone of treatment for both ES and SBS—the stricture can be deemed recalcitrant. An estimated 3,000 children annually in the United States (US) have recalcitrant ES, typically secondary to surgical repair of atresia, caustic ingestion, or gastroesophageal reflux. In adults, esophageal stricture often arises after an esophageal resection in connection with esophageal cancer. An estimated 20,000 new cases of esophageal cancer are diagnosed in the US every year.

Stricture can occur elsewhere in the gastrointestinal tract. For example, in patients with Crohn's disease, strictures are common, and they may include both de novo strictures as well as strictures arising subsequent to an earlier resection. In Crohn's disease, stricture etiology often includes both inflammatory pathways and fibrosis. In Crohn's disease, stricture is usually characterized by significant narrowing of the lumen, usually accompanied by wall thickening. In Crohn's disease, a resection is often performed around the ileocecal valve; a stricture can arise at the site of an anastomosis performed to rejoin the two sections of the bowel after the resection. Over one million people in the U.S. have Crohn's disease or a related condition.

A surgeon or endoscopist can dilate a gastrointestinal tract stricture using a balloon or by another type of mechanical dilation. Dilation can provide transient relief, but can exacerbate scar tissue formation. Exacerbation of scarring can lead to recurrence of stricture. In children with esophageal stricture, serial dilations can negatively affect a child's psychosocial development.

Adjunct endoscopic therapies for stricture, such as injections of steroids or mitomycin C, have limited benefit and have potential undesirable complications.

Self-expanding stents and electrocautery incisional therapy similarly fail to achieve long-term resolution of stricture for many patients and have potential complications for many patients. Self-expanding stents can migrate from the position in which they were initially positioned, which can result in obstruction or perforation, both with potentially severe consequences for the patient.

Lumen-apposing stents originally designed for patients with pancreatic cysts can be used for stricture in the bowel and are less likely to migrate, but lack features and functionality to bring about resolution of the stricture.

Surgical options for stricture include stricturoplasty procedures, such as the Heineke-Mikulicz and the Finney technique, and procedures where a strictured segment is removed and the lumen (esophagus or bowel) sewn back together. For esophageal stricture, a segment taken from elsewhere in the gastroinstestinal tract can be used to replace a strictured segment of the esophagus. All of these are associated with tissue loss and complications such as re-stricture. Esophageal replacement surgery is usually a last resort treatment for ES and has particularly high associated morbidity and mortality.

If stricture interventions fail, a patient can be left with a permanent stoma. For the esophagus, this is known as a spit fistula.

Figure 4:
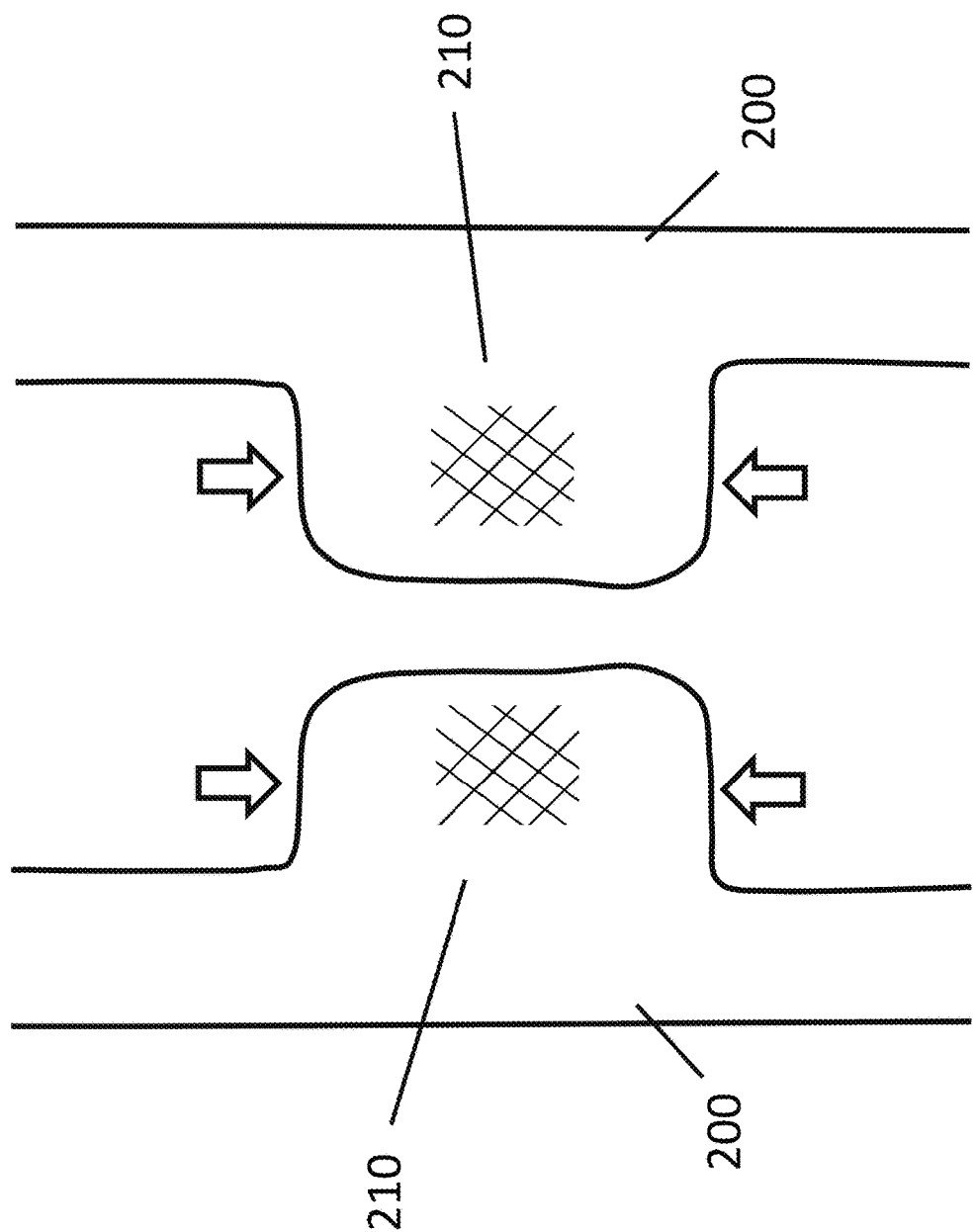
FIG. 4 illustrates the anatomy of the stricture of FIG. 3, illustrating the longitudinal compressive force, according to one or more embodiments.

Device systems can be designed to longitudinally compress a stricture. Springs and magnetic field effects can provide force to longitudinally compress a stricture. The term longitudinal is used to refer to compressive forces acting approximately in the direction of the stricture's length, as illustrated in FIG. 4. A stricture can be described by the length of the segment of lumen where there is significant narrowing of the lumen, usually accompanied by wall thickening, and by the cross-sectional area in the segment where there is significant narrowing of the lumen.

An anastomosis is a connection between two lumens in the body through which material can flow. For example, when a cancerous section of the colon is surgically removed, the joining together of the upstream section and the downstream section of the colon to restore continuity (i.e., to re-create a lumen through which material can flow) is referred to as surgically creating an anastomosis. Historically, GI tract anastomoses were created by hand-sewing. Later, a variety of staplers and other specialized device systems were developed to facilitate anastomosis creation. Where specialized device systems are used for anastomosis creation, the devices often comprise at least two components, where a first device component is positioned in a first lumen and a second device component is positioned in a second lumen. A surgeon brings the two device components in such a way that the two device components interact with each other and join the lumens.

For example, to create an anastomosis between the stomach and the small bowel for a duodenal obstruction, a surgeon may punch the anvil of a circular stapler through the stomach wall and then through a section of small bowel wall. The surgeon will then bring the anvil into the main part of the circular stapler and will then fire the staples.

Device systems can be designed with magnetic elements such that magnetic force can be leveraged in bringing two lumens together to create an anastomosis or to longitudinally compress a stricture. Some device systems use ring- or disk-shaped magnetic elements.

In practice, however, device systems with magnetic elements are not commonly used for anastomosis creation. One reason that magnetic force-based device systems have gained only limited traction for anastomosis creation is that, historically, these device systems have lacked features and functionality to accommodate challenging anatomy. For example, it can be difficult to bring magnetic device components through narrow regions of anatomy.

In practice, device systems for longitudinally compressing stricture tissue are not commonly used for treating stricture. One reason that longitudinal compression device systems have gained only limited traction for stricture treatment is that, historically, these device systems have lacked features and functionality to allow them to be used where the stricture can be readily accessed only from one side, for example where an esophageal stricture can be readily accessed only transorally or where a small bowel stricture can be accessed only transanally. For example, it can be difficult to pass a device component through the stricture itself in order to apply longitudinal compressive force.

In one embodiment, stents, including lumen apposing stents, can be used in patients with strictures in the gastrointestinal tract, with the intention of maintaining a sufficiently large opening of a stricture—that is, a segment of the gastrointestinal tract that has become narrowed—to allow for the passage of food and waste. In practice, stents that function by expanding radially outward, correspondingly forcing the mucosa radially outward, fail to bring about optimal outcomes in many patients. For example, as with balloon dilation, application of radial outward forces on a stricture by an expanding stent can exacerbate scar tissue formation. For example, self-expanding stents can migrate to another location in the gastrointestinal tract. Stents with large dual flanges, such as stents marketed as lumen-apposing stents, can have a lower likelihood of migration, but maintain the opening without having a therapeutic effect that can bring about an increase in patency greater than the dimensions of the stent's waist.

Figure 1A:
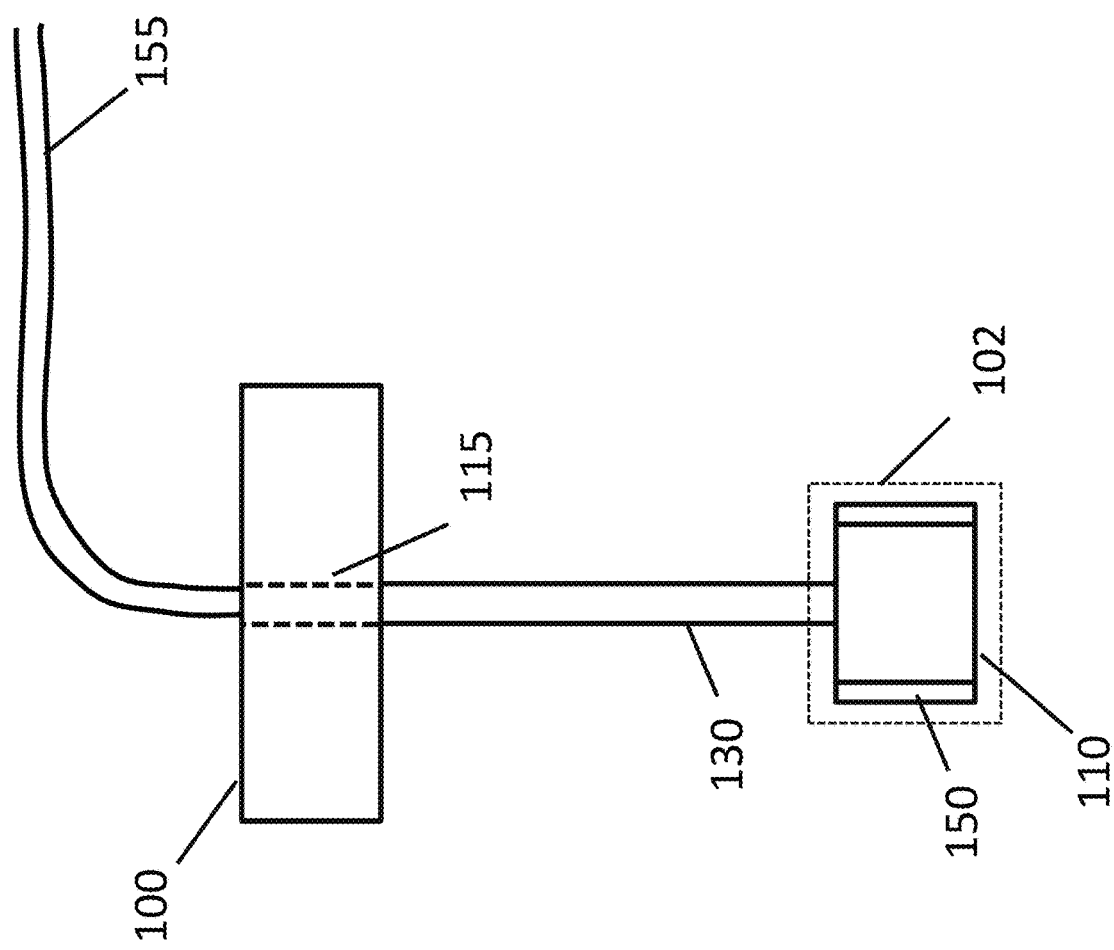

FIGS. 1A AND 1B illustrate a dual-flange stent, according to one or more embodiments. The dual-flange stent in FIGS. 1A AND 1B can have a therapeutic effect that can bring about a marked increase in patency and durable resolution of stricture. In one embodiment, FIG. 1A illustrates a cross-sectional view and FIG. 1B illustrates a plan view of the stent. The stent comprises a first flange 100 that can comprise a magnetic element. The stent further comprises a shaft 130 and a second flange 102 that can comprise a magnetic element. Specifically, the second flange 102 includes a core 110 and a balloon 150 attached to the core 110. The core 110 may include a magnetic element or may be a non-magnetic element. Attached to the core 110 is a balloon 150 that can be filled with saline or another fluid. In one instance, upon filling the balloon 150 with a fluid such as saline or another fluid, the balloon expands. The balloon 150 may expand rapidly. Thus, in one embodiment, the first flange 100 or the second flange 102 may be configured to transition between a first configuration and a second configuration, where the first configuration is compact (e.g., balloon 150 is in deflated state) and the second configuration (e.g., balloon 150 is in inflated state) provides a large tissue-compressing surface.

The balloon 150 can comprise materials including nylon, polyethylene terephthalate, or a low-durometer urethane. In one instance, the balloon can be blow molded. The balloon can be designed to expand radially. The balloon can be molded to have a surface that is approximately flat when, for example, the balloon 150 is an inflated state. The approximately flat surface can be oriented approximately perpendicular to the direction of expansion. The approximately flat surface can transition to a curved or beveled surface near the periphery or edge of the balloon 150. A curved or beveled surface near the periphery can be conducive to peripheral tissue healing in stricture treatment. A curved or beveled surface near the periphery can be conducive to device detachment after an intended therapeutic effect has been achieved. The diameter of the approximately flat surface (e.g., when inflated state) can be between 8 mm and 14 mm for a device for treating esophageal stricture in pediatric patients. The diameter of the approximately flat surface can be between 14 mm and 24 mm for a device for treating esophageal stricture or small bowel stricture in adults. The balloon can have at least one structural element that confers additional stiffness in its expanded state. The structural element that confers additional stiffness can include a polymer material. In several embodiments, the polymer can be selected from the group including parylene A, parylene AM, parylene C, ammonia and/or oxygen treated parylene C, and parylene C treated with either polydopamine, vitronectin, retronectin, or matrigel. The device can include a heating element for polymerizing a structural element that confers additional stiffness to the balloon. The device can include a light source for polymerizing a structural element that confers additional stiffness to the balloon. The structural element that confers additional stiffness can be metal wire. The metal wire can be a nickel-titanium or other superelastic or shape memory metal wire. The additional stiffness can be conferred with respect to force applied normal to portions of the face of the balloon located at or near the periphery of the balloon face In some embodiments, the stent can include more, fewer, or different components than those shown in FIGS. 1A and 1B.

The dual-flange stent in FIGS. 1A AND 1B can comprise at least one polymer resin. The polymer resin can flow into the balloon to cause the balloon to expand radially. In one embodiment, the resin can be a combination of bisphenol A dimethacrylate, 2-hydroxyethyl methacrylate, and urethane dimethacrylate. The polymer resin can be polymerizable through application of light, heat or directed acoustic energy.

Figure 2B:
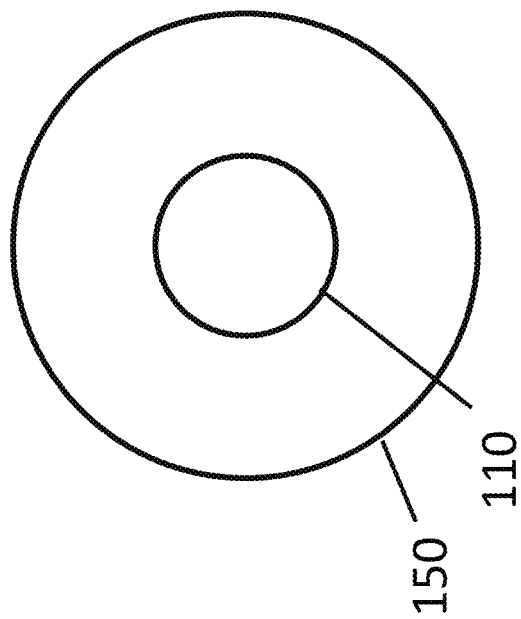
FIGS. 2A AND 2B illustrate the dual-flange stent of FIGS. 1A AND 1B, with the balloon that comprises the second flange expanded, according to one or more embodiments.
Figure 2A:
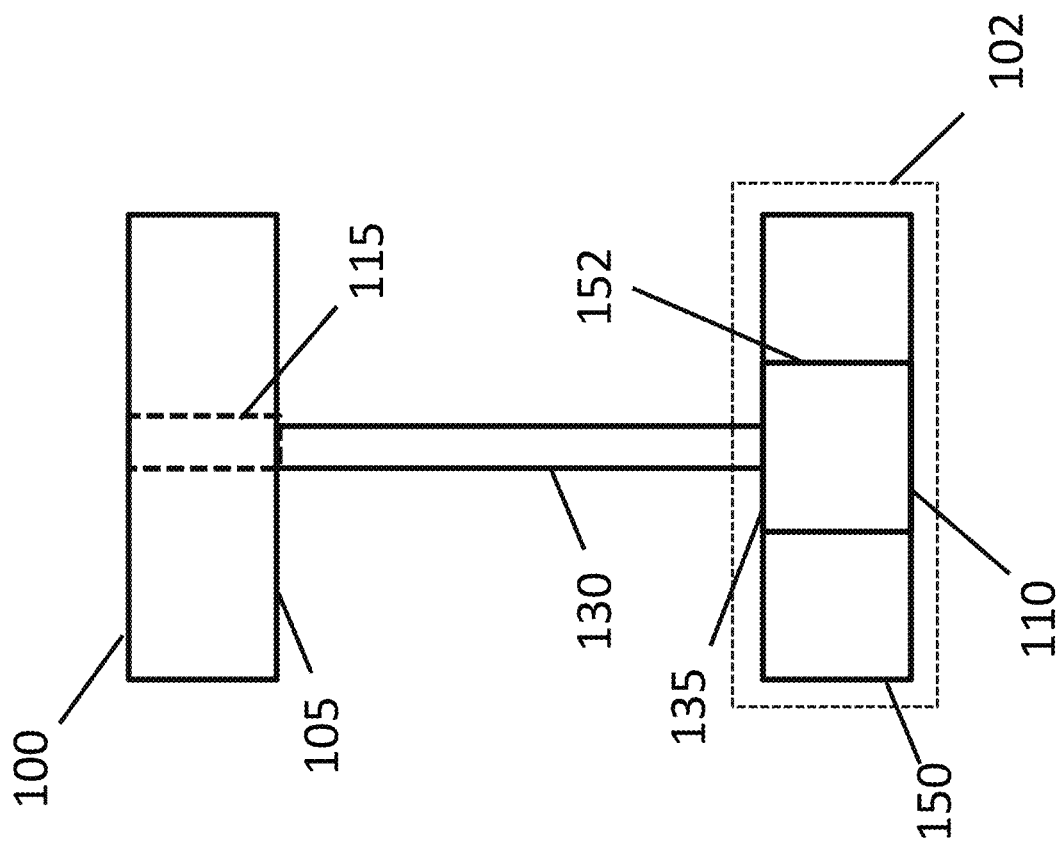

FIGS. 2A AND 2B illustrate the dual-flange stent of FIGS. 1A AND 1B, with the balloon 150 that comprises the second flange expanded, according to one or more embodiments. In one embodiment, FIG. 2A illustrates a cross-sectional view and FIG. 2B illustrates a plan view of the stent with the second flange expanded. An example of the expanded balloon 150 is illustrated in FIGS. 2A AND 2B. Once the balloon 150 has expanded, flanges 100 and 102 can be drawn together to compress interposed tissue. In the embodiment in which flanges 100 and 102 comprise magnetic elements, there can be an attractive force between the flanges 100 and 102 that allow the flanges 100 and 102 to be drawn together. However, it is appreciated that in other embodiments, the flanges 100 and 102 can be drawn together by any type of mechanism other than magnetic elements. For example, flanges 100 and 102 can also be drawn together by a mechanism that shortens shaft 130, such as a telescoping structure where a smaller tube of the shaft slides within a larger tube, or a collapsing feature of the shaft. The telescoping structure can comprise a voice coil actuator or another actuator mechanism. As another example, flanges 100 and 102 can also be drawn together by a mechanism that causes the connecting shaft 130 to translate through opening 115. As yet another example, flanges 100 and 102 can each comprise elements that generate an attractive force between the elements (other than those comprising magnets).

Figure 3:
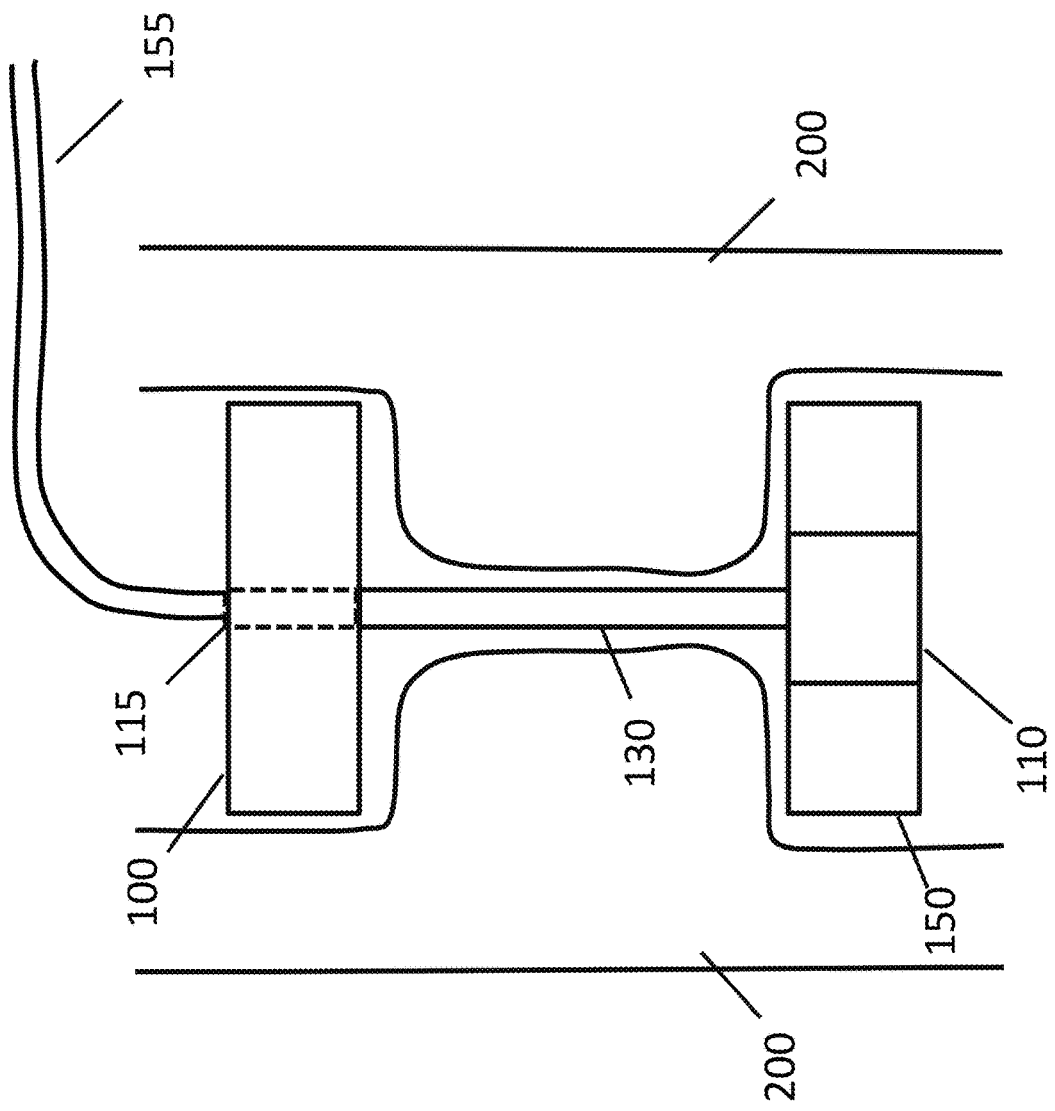
FIG. 3 illustrates the dual-flange stent of FIGS. 1A AND 1B, illustrating the anatomy of a stricture on which the flanges can apply longitudinal compressive force, according to one or more embodiments.

FIG. 3 illustrates the dual-flange stent of FIGS. 1A AND 1B, including the anatomy of a stricture 200 on which the flanges can apply longitudinal compressive force, according to one or more embodiments. If the stent has been positioned where the first flange 100 is on one side of a stricture and the second flange 102 is on the other side of a stricture, as shown in FIG. 3, the tissue-contacting face 105 of the first flange 100 and the tissue-contacting face 135 of the second flange 102 can apply compressive force on tissue comprising the stricture.

FIG. 4 illustrates the directionality and other aspects of the application of force on the tissue comprising the stricture by the dual-flange stent of FIGS. 1A AND 1B, according to one or more embodiments. Strictures can comprise fibrotic tissue. Dilating a stricture with a balloon or otherwise mechanically dilating a stricture can exacerbate the stricture by causing injury in and around fibrotic tissue comprising the stricture.

Compression of fibrotic tissue can cause necrosis of the fibrotic tissue. Necrosis of fibrotic tissue can lead to favorable outcomes for patients. For example, in neonates with the congenital condition esophageal atresia, fibrotic tissue can be present in and around the esophageal pouches. Compression of this fibrotic tissue between flange-like components can be conducive to the establishment of a healthy esophagus. For example, the success of magnetic anastomosis devices (such as those described in U.S. Pat. No. 8,142,454, which is incorporated by reference in its entirety) is believed to be associated with compression of fibrotic tissue.

It can be understood that the first flange 100 and the second flange 102 of the device illustrated in FIG. 1A, FIG. 2A, and FIG. 3 can longitudinally compress the stricture, including fibrotic tissue 210 comprising the stricture.

In some embodiments, the system can comprise a catheter 155. In one instance, the catheter can comprise thermoplastic materials. The catheter can be polyether etherketone. The catheter can be a braided material. The catheter can reversibly attach to the first flange 100 or the second flange 102. The shaft 130 can have an inner lumen and an outer lumen and the distal end of the catheter 155 can pass within the inner lumen of the shaft 130. For example, the catheter can attach to a top surface of the first flange 100 or to any portion of the first flange 100. As another example, the catheter can pass through the inner lumen of the shaft 130 and latch to an inner surface of the shaft 130. For example, a latching mechanism can maintain the catheter within the inner lumen of the shaft or the stent. As yet another example, the catheter can pass through the inner lumen of the shaft 130 and attach to the inner surface of the second flange 102 or go through an opening of the second flange 102 and anchor to a bottom surface of the second flange 102 using, e.g., a butterfly latch mechanism. However, it is appreciated that in other embodiments, the catheter can also be attached to an outer lumen of the shaft 130. A control mechanism at or near the proximal end of the catheter can engage or disengage the latching mechanism. In some embodiments, the system comprises an endoscope and the stent and catheter can pass through the working channel of the endoscope. The stent and catheter can be back-loaded into the working channel of the endoscope. The stent can have a flange in a first configuration (e.g. balloon 150 in a deflated state) that can pass through the stricture while the remaining flange remains on the proximal side of the stricture.

Referring back to FIGS. 1A and 1B, with the balloon 150 in its deflated state, the outside diameter of the second flange 102 can be smaller than the outside diameter of the first flange 100. For example, in a hypothetical esophageal stricture patient where healthy segments of the esophagus can readily pass a catheter with an outside diameter of 15 mm, while at a segment of the esophagus that has strictured, the maximum diameter of a catheter that can pass through the stricture may only be 6 mm. For example, in one embodiment, the second flange 102 may include a core 110 and a balloon 150 surrounding side surfaces 152 of the core 110. For a magnetic element comprising the core 110 having an outside diameter of 5 mm and the added thickness of the deflated balloon 0.5 mm, the second flange 102 with deflated balloon 150 can be passed through the stricture, with the first flange 100 remaining on the proximal side of the stricture (for a stricture accessed transorally). Thus, the collapsed or deflated state of the balloon allows the second flange 102 to be sufficiently reduced in size to pass through the narrowed portion of the stricture such that the second flange can be positioned on the opposite side of the stricture relative to the first flange 100. With inflation of the balloon 150 such that the second flange 102 reaches a diameter of 15 mm, longitudinal compression is applied on both sides of the stricture by the two flanges in a manner that can be conducive to achieving patency with an opening of approximately 15 mm, with the fibrotic tissue 210 experiencing this longitudinal compression.

A favorable therapeutic effect can be achieved where the tissue-contacting faces of the two flanges can draw closer together as therapy progresses. An opening 115 in the first flange 100 or second flange 102 can allow for a progressively greater length of the shaft 130 to pass through a flange, such that the tissue-contacting faces can draw closer together.

Figure 5:
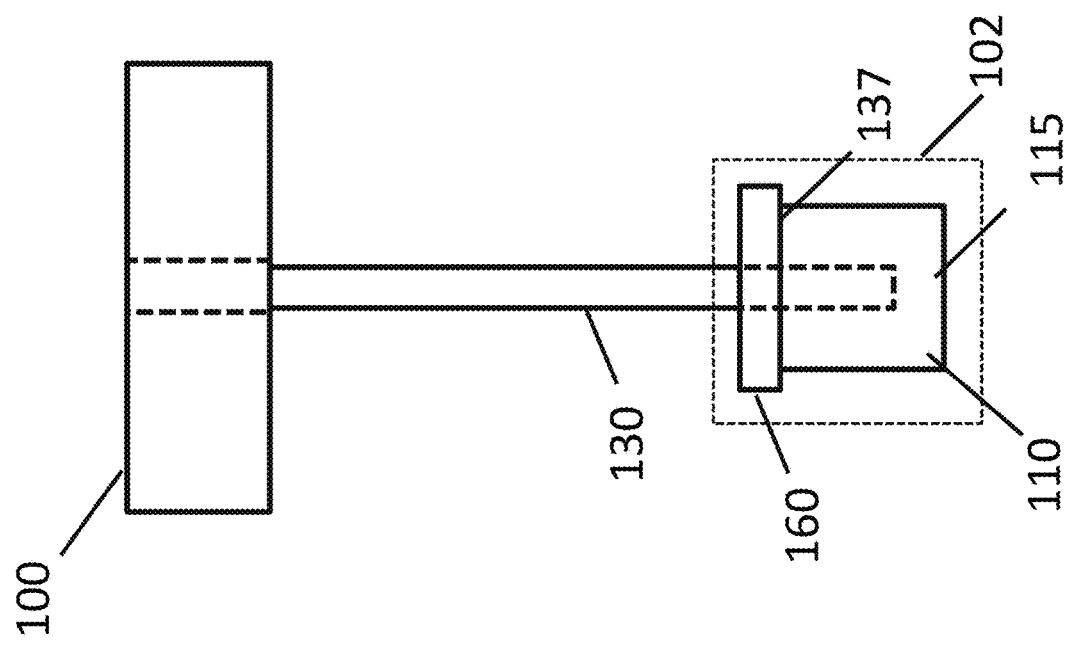
FIG. 5 illustrates a dual-flange stent with a first flange comprising a magnetic element and a second flange comprising a magnetic element and a balloon, where the balloon is positioned on a face of a magnetic element and where deflating the balloon can facilitate passing the second flange through a stricture, according to one or more embodiments.
Figure 6:
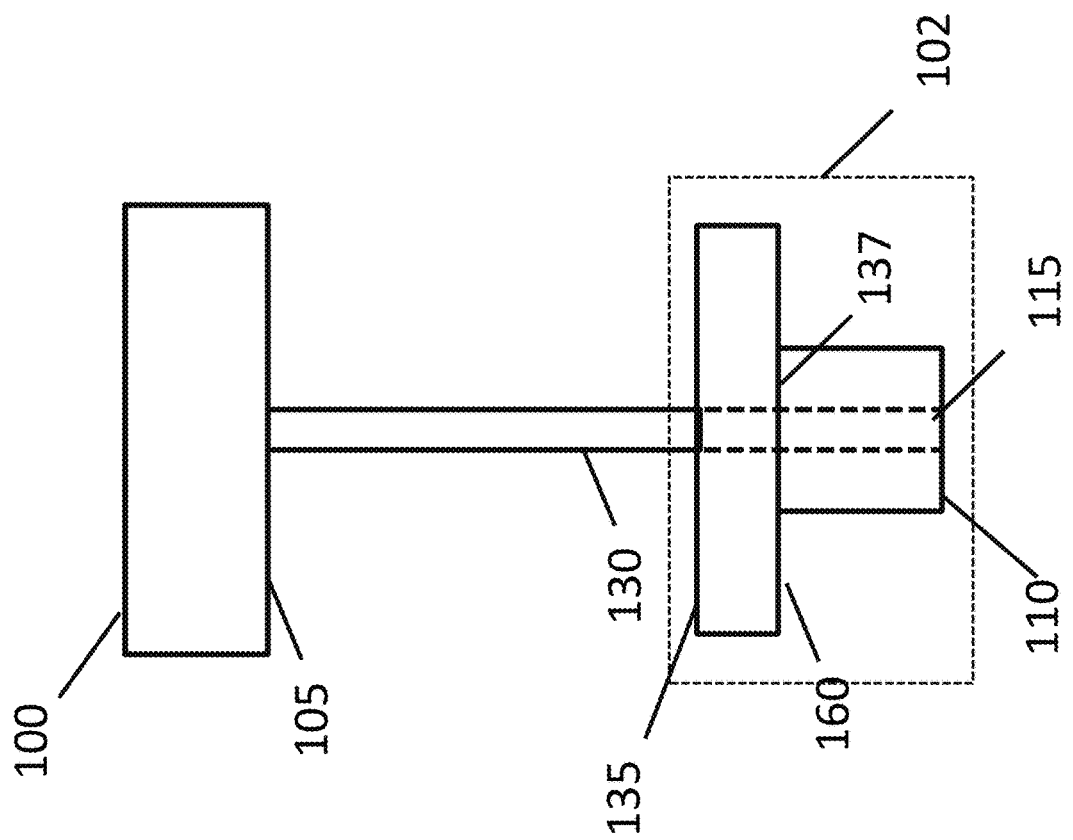
FIG. 6 illustrates the dual-flange stent of FIG. 5 with the balloon that includes the second flange expanded, according to one or more embodiments.

FIG. 5 illustrates a device for longitudinal compression of a stricture where a balloon 160 is attached on a face 137 of the core 110, according to one or more embodiments. FIG. 6 illustrates inflation of a balloon 160 on the face 137 of the core 110, where the balloon 160 can apply force on a stricture, according one or more embodiments. The stent of FIGS. 5 and 6 may be different from the stent described in conjunction with FIGS. 1A-3 in that the balloon 160 is disposed on the face 137 of the core 110 rather than surrounding the side surface of the core 110. Similar to the stent described in conjunction with FIGS. 1A-3, the stent of FIGS. 5-6 can be positioned where the first flange 100 is on one side of a stricture and the second flange 102 is on the other side of a stricture. With inflation of the balloon 160 to transition the flange 102 to a second configuration that provides a large tissue-compressing surface, longitudinal compression is applied to the stricture, such that the tissue-contacting face 105 of the first flange 100 and the tissue-contacting face 135 of the second flange 102 (e.g., an inner surface of the balloon 160 in FIG. 6) can apply compressive force on tissue comprising the stricture.

Figure 7:
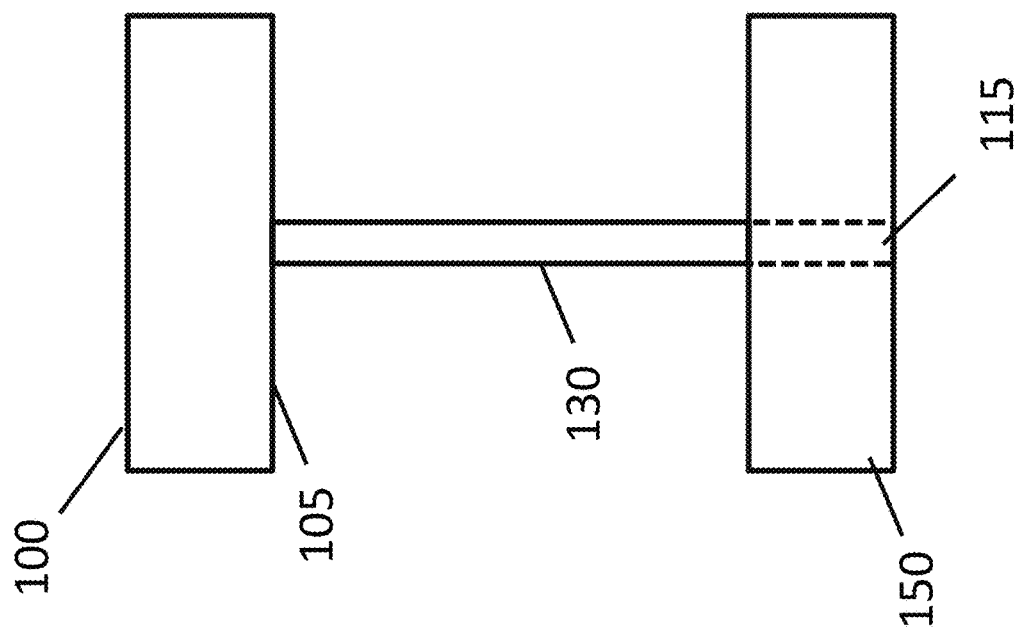
FIG. 7 illustrates a dual-flange device where a second flange comprises a balloon, according to one or more embodiments.

FIG. 7 illustrates a dual-flange device where a second flange comprises a balloon 150, according to one or more embodiments. In such an embodiment, the balloon 150 itself may constitute the second flange 102. In one embodiment, the balloon 150 can be filled with a ferrofluid. Upon filling the balloon 150 with a ferrofluid, the dual-flange can longitudinally compress a stricture due to the attraction force between a magnetic element included in the first flange 100 and the balloon 150 with the ferrofluid. The balloon 150 can be filled with a material that is polymerizable.

In any of the expandable devices with a balloon described herein, fluid can be introduced into a balloon by any of a variety of fittings and fluid introduction devices. A one-way valve can be incorporated into the device through which fluid can be introduced into a balloon and that can retain fluid within a balloon. A screw-on fitting can hold a fluid filling apparatus against an expandable device while fluid is introduced into a balloon. A variety of clamping fittings can hold a fluid filling apparatus against an expandable device while fluid is introduced into a balloon.

In any of the dual-flange devices described herein, fluid can be removed from a balloon after a period of time. Removal of fluid from a balloon after a stricture has resolved can be conducive to removal of the dual-flange device from the patient. For a balloon filled with saline, the balloon can be punctured to allow saline to be released into the gastrointestinal tract. For a balloon filled with another fluid, the fluid can be removed by a fitting. When the balloon is deflated, the second flange 102 is again reduced in size so that it can slide back through the opening and the device can be removed.

Figure 8:
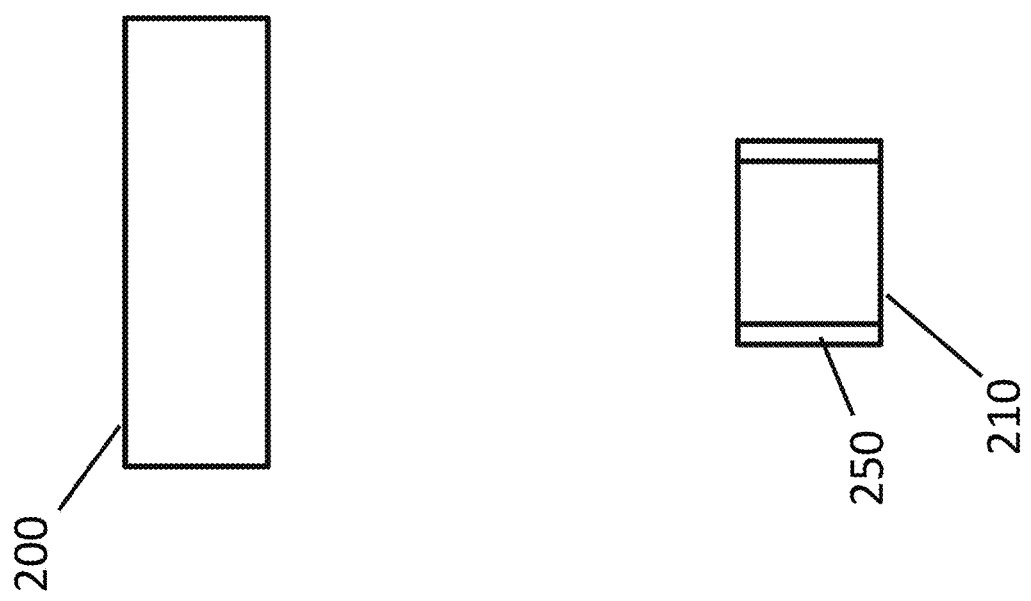
FIG. 8 illustrates a device for anastomosis creation or stricture treatment with a first anchor including a magnetic element and a second anchor comprising a magnetic element and a balloon, according to one or more embodiments.

FIG. 8 illustrates an anastomosis device with a first anchor 200 including a magnetic element and a second anchor comprising a magnetic element 210 and a balloon 250, according to one or more embodiments. The balloon 250 can be inflated once the second anchor is in position, for example, in the lower esophageal pouch for a patient where the anastomosis device is being used to repair esophageal atresia. With the balloon 250 in a deflated state, passage of the second anchor through narrow regions of the patient's anatomy can be easier and safer than it would be for an anchor that lacks a balloon that can be deflated. The esophageal stricture is an example of narrow anatomy where it is narrower relative to other portions of the anatomy, such as narrower than the rest of the esophagus.

Figure 9:
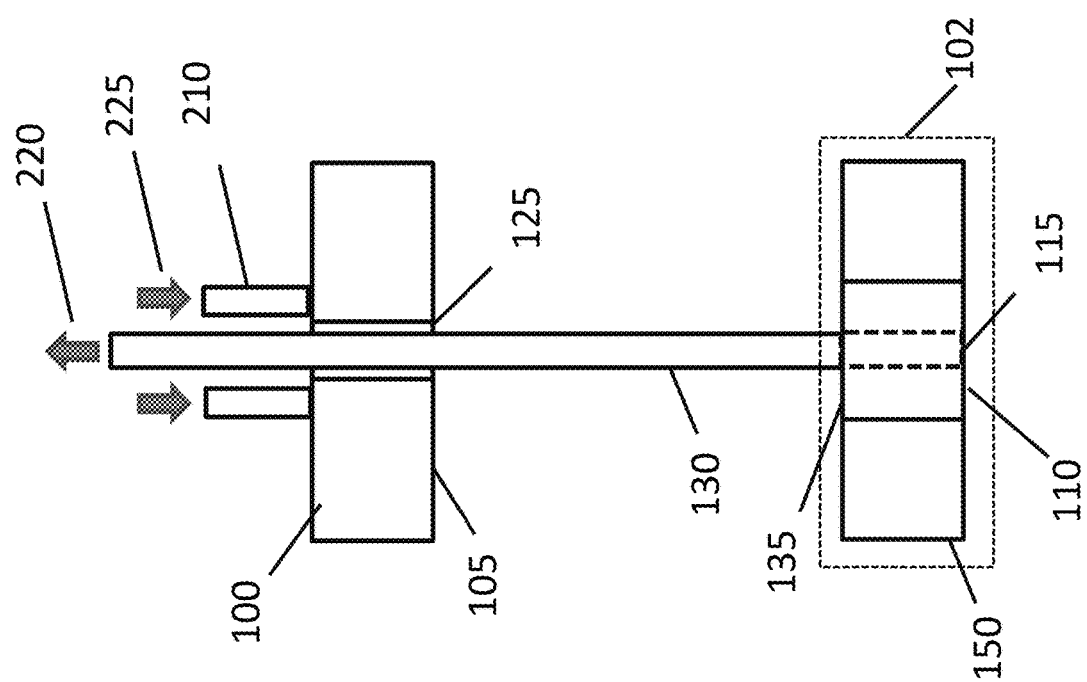
FIG. 9 illustrates a dual flange device comprising an actuator for drawing the flanges together to compress interposed tissue, according to one or more embodiments.

FIG. 9 illustrates a stent incorporating an apparatus for drawing the flanges together, according to one or more embodiments. The first flange 100 may be formed with an opening 125. The second flange 102 includes the core 110 and a balloon 150 attached to the core 110. A linear actuator 210 in contact with the first flange 100 applies force 220 to shaft 130, such that the shaft 130 translates upward (in the view of the drawing) through the opening 125 and the first flange 100 is pushed toward the second flange 102 to compress the interposed tissue. This in turn may cause the actuator 210 and the first flange 100 to move 225 toward the second flange 102. While FIG. 9 illustrates an embodiment in which the actuator 210 is attached to the first flange 100, it is appreciated that in other embodiments, the actuator 210 may be attached to the second flange 102, such that the shaft 130 translates downward (in the view of the drawing) through the opening 115 and the second flange 102 is pushed toward the first flange 100 to compress the interposed tissue. In some embodiments, actuators 210 may be disposed on both flanges 100 and 102 such that each flange is pushed toward the other flange simultaneously. Thus, in the embodiment of FIG. 9, the stent may include a linear actuator 210 for applying a force to the first flange 100 such that the first flange 100 is pushed toward the second flange 102. In such an embodiment, the first flange 100 or the core 110 of the second flange 102 may be comprised of non-magnetic material. The linear actuator 210 can be a voice coil actuator, a piezoelectric actuator, a piezoelectric motor, a solenoid, or another kind of linear actuator. The linear actuator 210 can be located on or near a flange can be located on or near the distal end of a catheter. The linear actuator 210 may further include an integrated potentiometer for measures actuation. In another embodiment, a discrete potentiometer or other displacement or velocity or acceleration sensor measures actuation.

Figure 10:
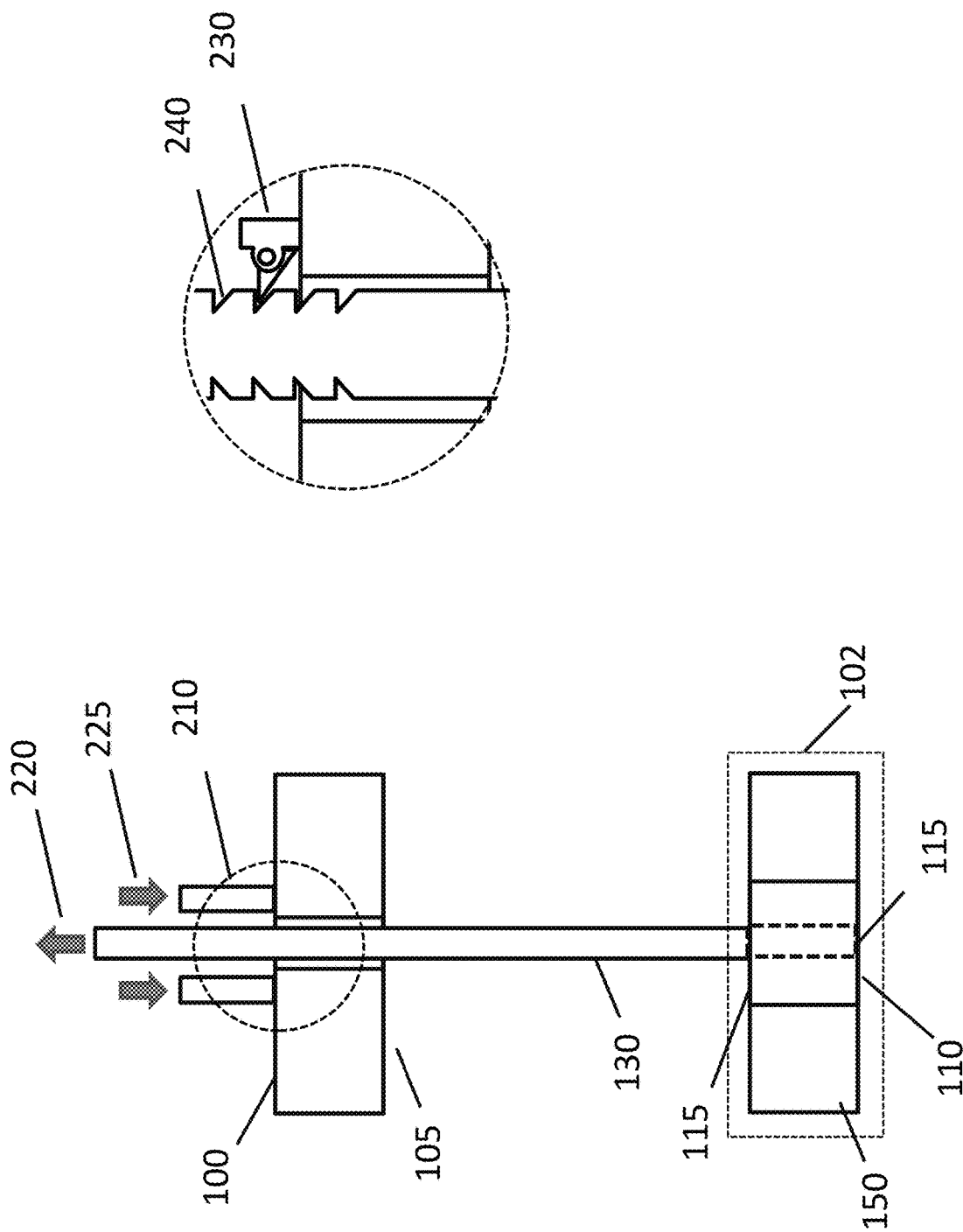
FIG. 10 illustrates a dual flange device comprising a ratcheting mechanism, according to one or more embodiments.

FIG. 10 illustrates a stent incorporating a ratchet mechanism 230, according to one or more embodiments. In one embodiment, the shaft 130 is formed with one or more features 240. In one instance, the features 240 on the shaft 130 may be one or more groove patterns formed on the surface of the shaft 130. The first flange 100 may be formed with the ratchet mechanism 230. The ratchet mechanism 230 may be, for example, a protrusion pattern configured to fit within a feature 240. The ratchet mechanism 230 can engage with features 240 on the shaft 130. In one instance, translation of the shaft 130 in the upward direction (in the view of the drawing) relative to the flange 100 can compress interposed tissue. The ratchet mechanism 230 can retain the flanges to bring about necrosis of interposed tissue. While FIG. 10 illustrates an embodiment in which the ratchet mechanism 230 is formed on the first flange 100, it is appreciated that in other embodiments, the ratchet mechanism 230 may be formed on the second flange 102, or both the first flange 100 and the second flange 102. Instead of a ratchet mechanism with groove patterns, living hinges or other elastomeric structures can apply friction that opposes translation of the shaft to have an equivalent effect of a ratcheting mechanism.

Figure 11B:
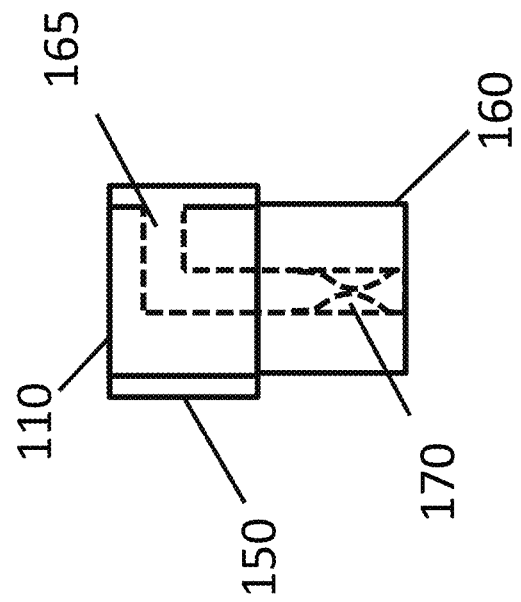
FIGS. 11A and 11B illustrate a device comprising a magnetic element and a balloon, where a balloon is positioned circumferentially on an element and where deflating a balloon can facilitate passing the device through narrow or tortuous anatomy, according to one or more embodiments.
Figure 11A:
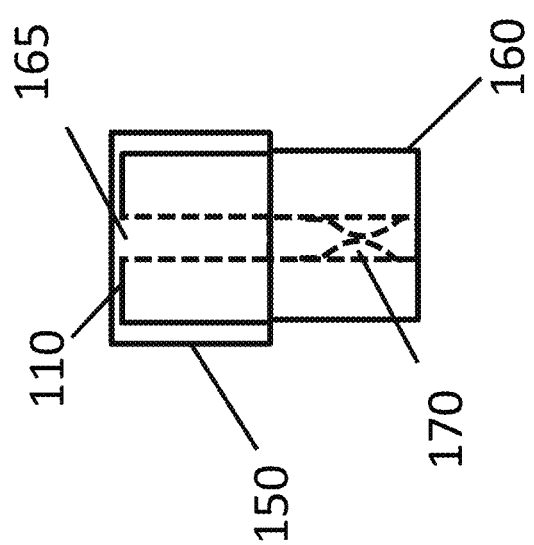

FIGS. 11A and 11B illustrate an expanding device comprising a flange 102 that can comprise a core 110 which can be a magnetic element. The flange 102 can also comprise a balloon 150 attached to the core 110 that can be filled with saline or another fluid. In one instance, upon filling the balloon 150 with a fluid such as saline or another fluid, the balloon expands. The balloon 150 may expand rapidly. The balloon 150 can comprise materials including nylon, polyethylene terephthalate, or a low-durometer urethane. The expanding device can comprise a fitting 160 to which a filling apparatus can be attached for filling the balloon 150. The core 110 can comprise at least one hole 165 through which fluid can flow into the balloon. The fitting 160 can comprise an elastomeric valve 170 that admits a lumen. Fluid can pass through the lumen and into the balloon 150. Upon withdrawing the lumen, the elastomeric valve can retain the injected fluid. The valve 170 can be a septum and the lumen can be a needle that punctures the septum. The valve 170 can be a needle valve or a ball valve or another mechanical valve. FIG. 11A illustrates that the at least one hole 165 is formed on a top portion of the core 110, while FIG. 11B illustrates that the at least one hole 165 is formed on a side portion of the core 110.

FIG. 12 shows photographs of devices with flanges comprising balloons that can radially expand, according to one or more embodiments. These devices can compress larger areas of interposed tissue in their expanded configurations than in their unexpanded configurations.

Figure 13C:
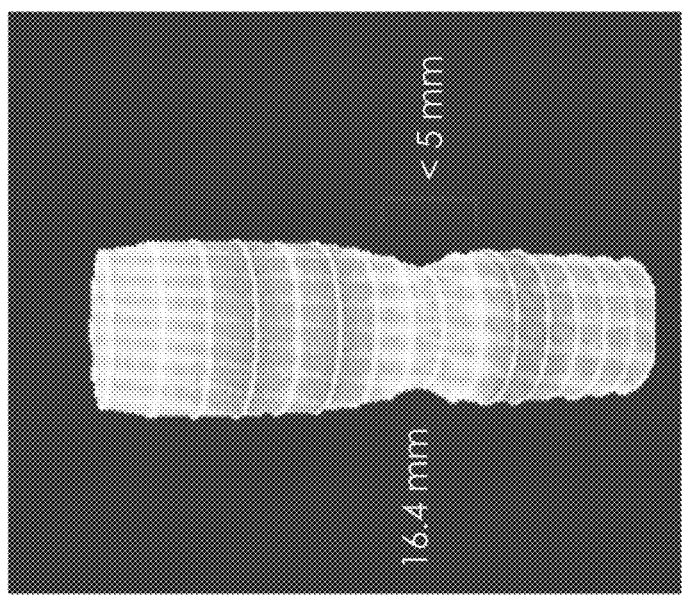
FIGS. 13A-13C illustrate the response of a stricture to longitudinal compression therapy.
Figure 13B:
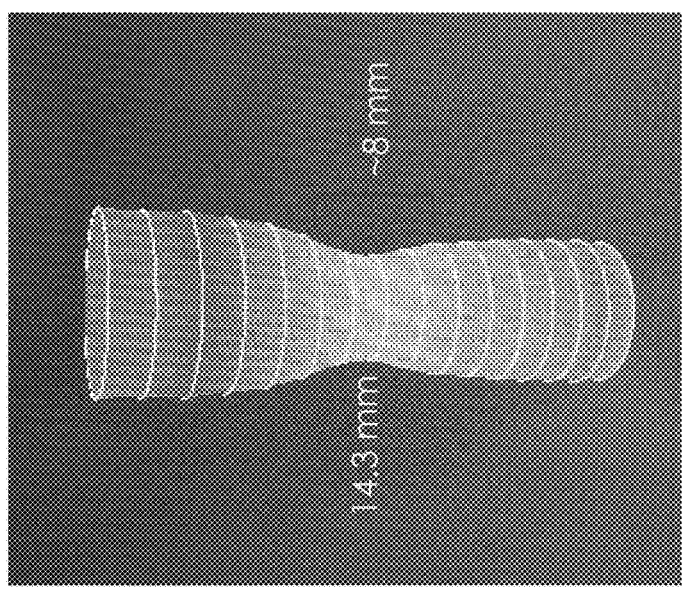
Figure 13A:
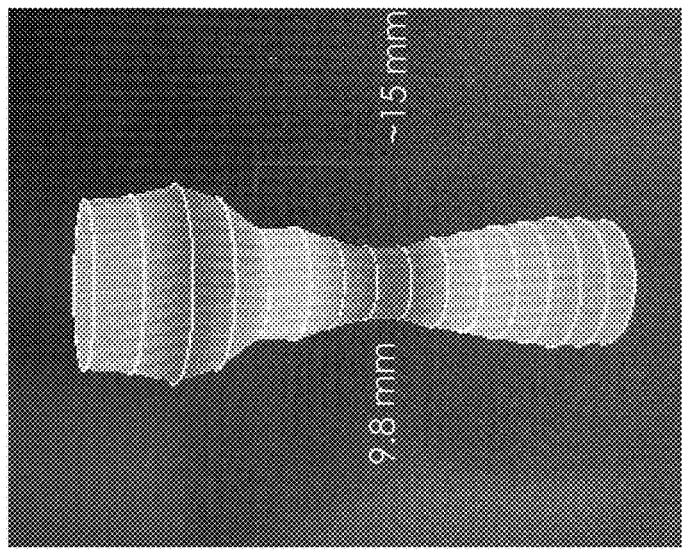

FIGS. 13A-13C illustrate the therapeutic effect of longitudinal compression in an animal model of stricture. The images depict the lumen cross-sectional area at regular intervals along the length of a segment of bowel in an animal model of stricture. The measurements of lumen cross-sectional area were made using an impedance-based method (Endoflip, Medtronic). FIG. 13A depicts the anatomy of a stricture prior to longitudinal compression therapy. The length of the stricture is approximately 15 mm and at its narrowest point, the lumen has a diameter of only 9.8 mm. FIG. 13B depicts the anatomy of the same stricture 2 weeks after longitudinal compression therapy using devices with 21 mm diameter flange components. FIG. 13C depicts the anatomy of the same stricture 9 weeks after longitudinal compression therapy. It is generally favorable for the patient where, after treatment, the lumen is enlarged, and the length of the stricture has lessened. At t=9 weeks, many strictures treated with balloon dilation will have recurred or be on a path to recurrence. In contrast, after longitudinal compression therapy, the treatment appears to be durable, with the lumen even more open than it was at t=2 weeks.

FIG. 14 illustrates a dual-flange stent with a second flange 102 comprising a wire mesh 138. The wire mesh 138 has an expanded configuration as shown in FIG. 14. The wire mesh 138 can comprise a shape memory alloy. The wire mesh 138 can be formed in the expanded configuration and heat treated to set the expanded configuration. The wire mesh 138 can also assume a configuration where it is elongated and flattened against the shaft 130. A latch mechanism can retain the wire mesh 138 in the elongated and flattened configuration. After passing the section of the shaft 130 with the wire mesh 138 in the elongated and flattened configuration, the latch can be released and the wire mesh 138 can assume the expanded configuration. A ratchet mechanism can draw the two flanges together to compress a stricture, similar to that described with respect to FIG. 10.

FIG. 15 illustrates a dual-flange stent with a latch mechanism. The first flange 100 comprises a first latch mechanism component 180 and the second flange 102 comprises a second latch mechanism component 185. The description of similar components as the previous figures are omitted for the sake of brevity. As stricture treatment progresses and the distance between the tissue-contacting flange faces decreases, the latch mechanism components can engage with one another. The stricture tissue can remain compressed between the latched flanges with the ratchet mechanism detached. Other components of the dual flange stent can be removed, leaving the latched flanges in place. The latched flanges can remain in place while fibrotic tissue undergoes necrosis and while peripheral tissue heals. The timescale for peripheral tissue healing can be between 5 days and 30 days. The flanges can comprise bioabsorbable or bio-degradable material, typically a biodegradable polymer, such as poly-L-lactic acid (PLLA), polyethylene glycol modified polycaprolactone, PLGA, gelatin-modified silicone, or an anhydride polymer. For treatment of a small bowel stricture, the biodegradable polymer can pass with feces.

FIG. 16 illustrates an anastomosis device with a first anchor 200 comprising at least one force sensor 220. The force sensor 220 can be a thin film force sensor. Reading the force sensor 220 can provide information about the progression of anastomosis formation or stricture treatment.

While embodiments herein are described primarily with respect to a dual-flange structure, it is appreciated that in other embodiments, the stent or anastomosis device may have any number of flange structures as appropriate, and one skilled in the art can devise alternative structural and functional designs through the disclosed principles, structures, and functionalities described herein.

Figure 17:
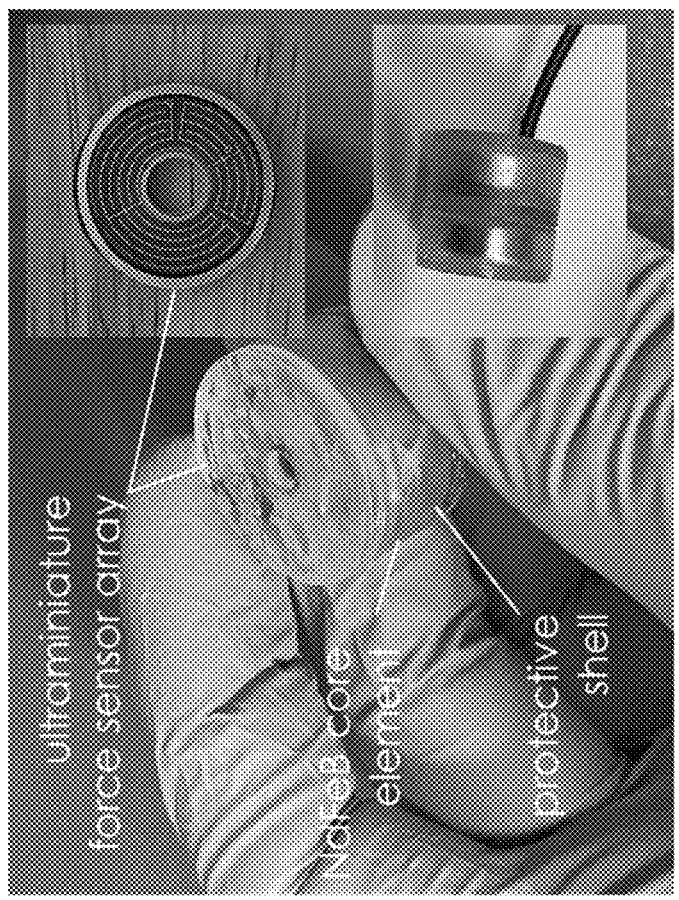
FIG. 17 illustrates a photo of a stricture treatment device with integrated force sensors, according to an embodiment.

FIG. 17 illustrates a photograph of a stricture treatment device, according to an embodiment, with integrated force sensors. The device also comprises a Bluetooth radio and circuitry. For example, the Bluetooth radio and circuitry may be used to transmit readings of the force sensor 220.

FIG. 18 illustrates photographs of stricture treatment using longitudinal compression. The large opening 310 was a badly strictured region of the anatomy prior to treatment. The necrosed tissue 315 was fibrotic tissue constituting the stricture and was resected through the action of longitudinal compression.

Additional Configuration Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein.

Various modifications, changes and variations, which will be apparent to those skilled in the art, may be made in the arrangement, operation and details of the method and apparatus disclosed herein without departing from the spirit and scope defined in the appended claims.

What is claimed is:

1. A stent, comprising:
    a first flange having a first surface configured to face a region of the anatomy that is tissue forming a stricture;
    a second flange configured to transition between an inflated state and a deflated state, the second flange having a second surface configured to face the region of the anatomy, wherein:
        in the deflated state, the second flange is further configured to allow for passage of the second flange through the stricture, wherein an outer diameter of the second flange is smaller than an outer diameter of the first flange in the deflated state, and
        in the inflated state, the second flange is configured to longitudinally compress the strictured tissue in the inflated state;
    a shaft connecting the first surface of the first flange and the second surface of the second flange; and
    an actuator mechanism on the first flange or the second flange, the actuator mechanism configured to apply force such that the first flange and the second flange at the inflated state are drawn together to longitudinally compress strictured tissue.

2. The stent of claim 1, wherein each of the first flange or the second flange comprises one or more magnetic elements.

3. The stent of claim 1, wherein the actuator mechanism is an actuator attached to the first flange or the second flange.

4. The stent of claim 1, wherein the second flange further comprises a core and a balloon attached to the core, wherein the second flange is at the deflated state when the balloon is deflated and the second flange is at the inflated state when the balloon is inflated.

5. The stent of claim 4, wherein the balloon is configured to inflate when a fluid is introduced into the balloon.

6. The stent of claim 5, wherein the fluid is saline fluid.

7. The stent of claim 4, wherein the balloon surrounds a side surface of the core.

8. The stent of claim 4, wherein the balloon is disposed on an inner surface of the core.

9. The stent of claim 1, wherein at least one of the first flange or the second flange is formed with a ratchet mechanism and the shaft is formed with one or more features, and wherein the ratchet mechanism is configured to engage with one or more features as the actuator mechanism applies the force.

10. The stent of claim 9, wherein the one or more features on the shaft are one or more groove patterns, and wherein the ratchet mechanism is a protrusion pattern configured to fit within the one or more groove patterns.

* * * * *